United States Patent [19]

Foulletier et al.

[11] Patent Number: 4,613,681
[45] Date of Patent: Sep. 23, 1986

[54] PROCESS FOR THE MANUFACTURE OF FLUORINATED ALKANOLS AND ESTERS THEREOF

[75] Inventors: Louis Foulletier, Oullins; André Lantz, Vernaison, both of France

[73] Assignee: Produits Chimiques Ugine Kuhlmann, France

[21] Appl. No.: 163,978

[22] Filed: Jun. 30, 1980

[30] Foreign Application Priority Data

Aug. 8, 1979 [FR] France ............................ 79 20280

[51] Int. Cl.$^4$ .................... C07C 69/003; C07C 67/00; C07C 31/38; C07C 29/58; C07C 29/124

[52] U.S. Cl. ........................... 560/236; 260/408; 560/20; 560/87; 560/111; 560/223; 568/842; 570/147; 570/155; 570/156

[58] Field of Search ................ 560/236, 111, 87, 20, 560/96, 204; 260/408; 568/842, 894

[56] References Cited

U.S. PATENT DOCUMENTS

| | | | |
|---|---|---|---|
| 3,171,861 | 3/1965 | Ahlbrecht | 568/842 |
| 3,812,008 | 5/1965 | Heywood et al. | 204/162 |
| 3,824,296 | 7/1974 | Schuierer | 568/842 |
| 4,001,309 | 1/1977 | Hayashi | 568/842 |
| 4,219,681 | 8/1980 | Schwenk | 568/842 |

OTHER PUBLICATIONS

Journal of the Chemical Society, Chemical Communications, vol. 21, Nov. 1, 1978, p. 919.
Journal of the American Chemical Society, Jul. 19, 1978, pp. 4888 and 4889.

Primary Examiner—Vivian Garner
Attorney, Agent, or Firm—Sigalos & Levine

[57] ABSTRACT

This invention relates to a process for the preparation of a fluorinated compound of the general formula

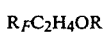

$R_FC_2H_4OR$ comprising reacting an iodide of the general formula $R_FC_2H_4I$ with a percarboxylic acid of the general formula $R^1CO_3H$ at a temperature and for a time sufficient to form said fluorinated compound; in said formulae $R_F$ is a straight or branched chain perfluorinated radical containing 1 to 20 C atoms, R is a hydrogen atom or —$COR^1$, and $R^1$ is a hydrogen atom or an aliphatic or aromatic hydrocarbon radical.

7 Claims, No Drawings

PROCESS FOR THE MANUFACTURE OF FLUORINATED ALKANOLS AND ESTERS THEREOF

BACKGROUND OF THE INVENTION

The present invention concerns a process for the preparation of 1, 1, 2, 2 - tetrahydro fluorinated alkanols and of the carboxylic acid esters of these alkanols. These products have the following general formulae:

$$R_F CH_2 CH_2 OH \text{ and}$$

$$R_F CH_2 CH_2 OCOR^1$$

in which $R_F$ represents a straight of branched chain perfluorinated radical containing from 1 to 20 carbon atoms and $R^1$ represents a hydrogen atom or an aliphatic or aromatic hydrocarbon radical.

Up to the present time, these products have been obtained according to the process described in French Pat. No. 1,380,579, by a reaction of the iodides, $R_F CH_2 CH_2 I$, with fuming sulfuric acid, followed by a hydrolysis of the sulfates having been formed. However, this process presents the disadvantages of furnishing large quantities of sulfuric diesters which are difficult to hydrolyze. According to the process described in U.S. Pat. No. 3,239,557, it is possible to obtain the esters $R_F C_2 H_4 OCOR^1$ by the conventional reaction of the iodides $R_F C_2 H_4 I$ with salts of the carboxylic acids $R^1 COOH$. The yields, however, are not very good, since larger or smaller quantities of olefins $R_F CH = CH_2$ are formed.

The alcohols can also be obtained according to the process of French Pat. No. 2,096,179, which consists of preparing the nitrates $R_F CH_2 CH_2 ONO_2$ by the reaction of the iodides $R_F CH_2 CH_2 I$ with nitric acid and of hydrogenating these nitrates in alcohol. This process, however, presents the drawback of necessitating two reaction stages, the last one of which must be carried out under a high hydrogen pressure.

French Pat. No. 2,180,113 describes a process for the production of mixtures of alcohol $R_F C_2 H_4 OH$ and of formates $R_F C_2 H_4 OCOH$ by the reaction, at high temperature, of iodides $R_F C_2 H_4 I$ with dimethyl formamide in the presence of a little bit of water. This process has the drawback of requiring very strict reaction conditions and of furnishing some olefin $R_F CH = CH_2$ as a by-product which diminishes the yield accordingly. A good selectivity in alcohol and formate can only be obtained by using very large quantities of dimethyl formamide.

SUMMARY OF THE INVENTION

The process of the present invention makes it possible to prepare fluorinated alkanols and/or esters from fluorinated iodides $R_F C_2 H_4 I$ in one stage at high yields.

Briefly, the present invention comprises a process for the preparation of a fluorinated compound of the following general formula:

$$R_F C_2 H_4 OR$$

comprising reacting an iodide for the general formula $R_F C_2 H_4 I$ with a percarboxylic acid of the general formula $R^1 CO_3 H$ at a temperature and for a time sufficient to form said fluorinated compound; in said formulae $R_F$ is a straight or branched chain perfluorinated radical, $C_n F_{2n+1}$, containing 1 to 20 C atoms, R is a hydrogen atom or $-COR^1$, and $R^1$ is a hydrogen atom or an aliphatic or aromatic hydrocarbon radical.

DETAILED DESCRIPTION

With the instant process, when the iodide, $R_F C_2 H_4 I$, is mixed with a peracid, $R^1 CO_3 H$, there is the immediate formation of iodine and the fluorinated compound is converted into an alkanol, $R_F C_2 H_4 OH$, into an ester $R_F C_2 H_4 OCOR^1$, or into a mixture of the two. The relative proportions of alkanol and of ester depend principally on the particular peracid and on the operating conditions; i.e., type of solvent, water content of the reaction medium, temperature, molar ratio of the reagents, and the like. From the disclosure given herein those skilled in this art can make the adjustments necessary to obtain the particular perfluoro compounds desired.

The peracids which can be used are, for instance, perbenzoic, para-nitroperbenzoic, chloroperbenzoic and perphthalic acid, but in general the more easily accessible aliphatic peracids are preferred, such as performic, peracetic, perpropionic or perbutyric acid. These peracids can be obtained according to the known preparation methods for these products. One of the preparation methods, which is especially simple, consists in using a mixture of hydrogen peroxide and of the carboxylic acid which furnishes the percarboxylic acid according to the following balanced reaction:

$$R^1 COOH + H_2 O_2 \rightleftharpoons R^1 CO_3 H + H_2 O.$$

Depending on the value of the ratio of $R^1 COOH/H_2 O_2$, the nature of the radical $R^1$, the quantity of water introduced with the reagents and depending on the temperature, a certain degree of conversion of the hydrogen peroxide into peracid is obtained. Thus, in the case of formic acid with 70% hydrogen peroxide at 20° C., the degree of conversion, at equilibrium, of the hydrogen peroxide into performic acid amounts to 70% for a molar ratio of $HCOOH/H_2 O_2$ of 3, to 82% for a molar ratio of 5, and to 95% for a molar ratio of 10. The rate of formation of the peracid from the acid and the hydrogen peroxide depends on the nature of the acid being used and the reaction can, as a rule, be accelerated by the introduction of slight amounts of a strong acid such as $H_2 SO_4$. In the case of strong organic acids such as, for instance, HCOOH or $CF_3 COOH$, the equilibrium can be attained rapidly without catalyst. The percarboxylic acids obtained by this method are perfectly suitable for the process of the invention, even if the conversion of the hydrogen peroxide into the peracid is not quantitative and if these mixtures still contain unconverted hydrogen peroxide.

The peracids obtained by any other process can likewise be used for the present invention.

The reaction of the invention is preferably carried out in a solvent medium. The solvent can be either the carboxylic acid from which the peracid has been prepared (HCOOH, $CH_3 COOH$, $CH_3 CH_2 COOH$, and the like) or another solvent which is inert towards the peracids, such as aromatic hydrocarbons, halogenated solvents ($CH_2 Cl_2$, $CHCl_3$, dichloroethane, trichloro trifluoro ethane, and the like), certain hydrocarbons or certain ethers (dioxane), and the like.

The reaction can be carried out by introducing the iodide $R_F C_2 H_4 I$ into the peracid, but with a view to reducing the decomposition of the peracid as much as possible, it is desirable to introduce the peracid into the iodide. The reaction temperature is not critical and the reaction can be carried out within a rather wide temperature range, but in general it is preferred for it to be carried out at temperatures close to the ambient temperature (15° to 45° C.)

Depending on the quantities of peracid utilized the iodine of the fluorinated iodide can be found at a higher degree of oxidation than that of elementary iodine, and hypoiodous and iodic acids can, in particular, be formed. This supplementary oxidation obviously consumes large quantities of peracids or of hydrogen peroxide, but it is possible to reduce this drawback by fixing the iodine as it is being formed. Out of the methods making it possible to fix the iodine consists of carrying out the reaction in the presence of an aromatic hydrocarbon capable of being iodinated, such as benzene, toluene, or xylene which is partially converted into an iodinated aromatic derivative according to the reaction:

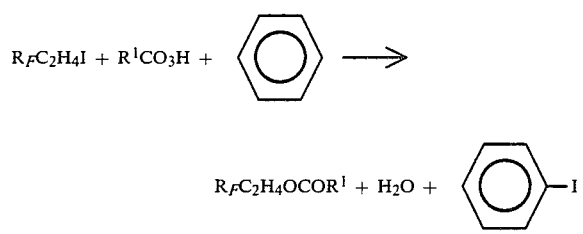

The fluorinated products formed are insoluble in water and can, as a rule, be separated by simple decantation after dilution of the reaction medium with water. This separation is preferably carried out after reduction of the iodinated derivatives by means of a conventional reducing agent such as sodium sulfite, for instance. When the reaction is carried out in the presence of a solvent which is immisicible with water, then this solvent can be separated from the fluorinated products by any appropriate technique, for instance by distillation.

The conversion of the iodide $R_fC_2H_4I$ into alcohols and esters takes place with excellent selectivities and the formation of by-products has not been observed. In particular, very little olefin $R_fCH=CH_2$ is formed. This is a by-product which, as a rule, is formed in large quantities during the course of most of the other production processes and which lowers their yields considerably.

The fluorinated esters $R_fC_2H_4OCOR^1$ and the fluorinated alcohols $R_fC_2H_4OH$ prepared according to the present process are useful raw materials for the production of surfactants and hydrophobic and oleophobic products. These products can, in particular, be easily converted into acrylic or methacrylic esters which permit the preparation, by polymerization, of hydrophobic and oleophobic agents for textile materials, leather or paper. The mixtures of esters $R_fC_2H_4OCOR^1$ and alcohols $R_fC_2H_4OH$ can likewise be converted into useful products. Thus, a mixture of alcohol $R_fC_2H_4OH$ and of formate $R_fC_2H_4OCOH$ can be converted into an acrylate by transesterification with methyl acrylate, for example. The mixture or alcohol and ester can also be entirely converted into alcohol by the hydrolysis of the ester, by saponification or by transesterification with methanol, for example.

The invention will be further described in connection with the following examples which are given for purposes of illustration only.

EXAMPLE 1

12 g of $C_6F_{13}C_2H_4I$ (0.025 moles) are introduced into a reactor containing 7.9 g of para-nitroperbenzoic acid (0.043 moles) and 50 ml of methylene chloride, while maintaining the temperature between 25° and 30° C. by external cooling with cold water. The mixture is kept at this temperature, under agitation, for 3 hours. 100 ml of water are then introduced and the liquid phase is analyzed by gas chromatography, Besides methylene chloride, the liquid phase contains a mixture of $C_6F_{13}C_2H_4OH$ and of $C_6F_{13}C_2H_4I$ in the following proportions:

$C_6F_{13}C_2H_4OH$: 52%
$C_6F_{13}C_2H_4I$: 48%

EXAMPLE 2

92 g of formic acid, 10 g of 70% hydrogen peroxide, and 1 g of sulfuric acid are introduced into an agitated reactor and this mixture is kept under agitation for 1 hour at 20° C. for the purpose of preparing some performic acid.

The resultant mixture is then added in 1 hour and 40 minutes to a mixture of 48 g of $C_6F_{13}C_2H_4I$ and 20 g of formic acid, while maintaining the temperature at 40° C. during the entire operation. The reaction medium is still kept at 40° C. for one hour after the addition has been completed and then 100 ml of water are introduced and the medium is decolorized by the addition of sodium sulfite. The lower phase is then decanted and washed twice with 50 ml of water. 41 g of a product containing the following compounds are thus recovered:

1%—$C_6F_{13}C_2H_4OH$
44%—$C_6F_{13}C_2H_4I$
53%—$C_6F_{13}C_2H_4OCOH$

The reaction mixture was analyzed by gas chromatography, after calibration with samples of the various pure products.

EXAMPLE 3

46 g of formic acid, 5 g of 70% hydrogen peroxide and 0.5 g of sulfuric acid are introduced into an agitated reactor and this mixture is kept under agitation for one hour at 20° C.

This solution is then allowed to run into a mixture of 24 g of $C_6F_{13}C_2H_4I$ and 20 ml of methylene chloride during a time period of 1 hour, while the temperature is maintained at 30° C. The reaction medium is still kept at 30° C. for 1 additional hour after the addition of the reactants has been terminated and then 50 ml of water are allowed to run in and sodium sulfite is added until complete decolorization of the iodine occurs. The lower phase is decanted and washed with 50 ml of water. The methylene chloride is then evaporated and 19 g of fluorinated product are recovered, containing:

3%—$C_6F_{13}C_2H_4OH$
35%—$C_6F_{13}C_2H_4I$
58%—$C_6F_{13}C_2H_4OCOH$

EXAMPLE 4

Example 2 is repeated except that the peracid obtained from:

HCOOH: 92 g
70% $H_2O_2$: 10 g
$H_2SO_4$: 1 g is introduced into a mixture of:
- $C_6F_{13}C_2H_4I$: 24 g
- HCOOH: 20 g.

After treatment, 19 g of product containing the following compounds are obtained:
- $C_6F_{13}CH=CH_2$: 0.1%
- $C_6F_{13}C_2H_4OH$: 2.6%
- $C_6F_{13}C_2H_4I$: 15%
- $C_6F_{13}C_2H_4OCOH$: 80%

EXAMPLE 5

A solution of performic acid is prepared by mixing 92 g of formic acid and 10 g of 70% hydrogen peroxide, and this mixture is kept at 20° C. for 1 hour and 30 minutes. This product is then allowed to run, under agitation, into a mixture of 48 g of $C_6F_{13}C_2H_4I$ and 20 g of formic acid during a time period of 2 hours, while maintaining the temperature at 25°–30° C. The mixture having been obtained is allowed to rest at 25° C. for 1 hour and then it is treated with water and sulfite. 40 g of product are obtained, containing:
- $C_6F_{13}C_2H_4OH$: 7%
- $C_6F_{13}C_2H_4I$: 14.8%
- $C_6F_{13}C_2H_4OCOH$: 76.5%

EXAMPLE 6

Example 2 is repeated, but the peracid solution is allowed to run into the $C_6F_{13}C_2H_4I$, while maintaining the temperature of the latter at 60° C. After treatment, 38 g of product are recovered, containing:
- $C_6F_{13}C_2H_4OH$: 1.3%
- $C_6F_{13}C_2H_4I$: 35%
- $C_6F_{13}C_2H_4OCOH$: 62%

EXAMPLE 7

Example 2 is repeated, but the $C_6F_{13}C_2H_4I$ is replaced by 37.5 g of $C_4F_9C_2H_4I$. After treatment, 28 g of product containing the following compounds are thus obtained:
- $C_4F_9C_2H_4OH$: 2%
- $C_4F_9C_2H_4I$: 36%
- $C_4F_9C_2H_4OCOH$: 60%

EXAMPLE 8

Example 2 is repeated, with the difference of replacing the iodide having an $R_F$ containing 6 carbon atoms by 53.7 g of an $R_FC_2H_4I$ composed of a mixture of the various homologs of $C_4F_9C_2H_4I$ to $C_{18}F_{37}C_2H_4I$ of the following composition by weight:
- $C_4F_9C_2H_4I$: 0.9%
- $C_6F_{13}C_2H_4I$: 51%
- $C_8F_{17}C_2H_4I$: 28.2%
- $C_{10}F_{21}C_2H_4I$: 11.5%
- $C_{12}F_{25}C_2H_4I$: 4.4%
- $C_{14}F_{29}C_2H_4I$: 1.7%
- $C_{16}F_{33}C_2H_4I$: 0.6%
- $C_{18}F_{37}C_2H_4I$: 0.2%

The mean molecular weight of this product is close to 534.

After reaction and treatment as indicated in Example 2, 45 g of product are obtained, containing approximately:
- $R_FC_2H_4OH$: 2%
- $R_FC_2H_4I$: 50%
- $R_FC_2H_4OCOH$: 46%

EXAMPLE 9

A solution of peracetic acid is prepared by keeping a mixture of 50 g of acetic acid, 5 g of 70% hydrogen peroxide and 0.5 g of sulfuric acid at 20° C. for 2 hours and 30 minutes. The mixture having been obtained is then added to 24 g of $C_6F_{13}C_2H_4I$ during a time period of 1 hour and 30 minutes, with the temperature being kept at 30° C. during the entire duration of the addition. The reaction medium is still kept at 30° C. for an additional one hour, and then it is treated with 100 ml of water and a sufficient quantity of sodium sulfite solution in order to decolorize it. After decantation and washing with water, 21 g of fluorinated product are obtained, which according to chromatographic analysis contains:
- $C_6F_{13}CH=CH_2$: 0.8%
- $C_6F_{13}C_2H_4OH$: 15%
- $C_6F_{13}C_2H_4I$: 45%
- $C_6F_{13}C_2H_4OCOH$: 37%

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for the preparation of a fluorinated alkanol, ester, or mixture thereof of the general formula $$R_FC_2H_4OR$$

comprising reacting an iodide of the general formula $R_FC_2H_4I$ with a percarboxylic acid of the general formula $R^1CO_3H$ at a temperature and for a time sufficient to form said fluorinated compound; in said formulae $R_F$ is a straight or branched chain perfluorinated radical containing 1 to 20 C atoms, R is a hydrogen atom or $-COR^1$, and $R^1$ is a hydrogen atom or an aliphatic or aromatic hydrocarbon radical.

2. The process of claim 1 in which the reaction is carried out in the presence of a solvent for said perfluorinated compound which is inert to the peracid.

3. The process of claims 1 or 2 in which the iodide is added to the percarboxylic acid.

4. The process of claims 1 or 2 in which the percarboxylic acid is added to the iodide.

5. The process of claims 1 or 2 in which the temperature is from about 15° to 45° C.

6. The process of claims 1 or 2 in which the percarboxylic acid is an aliphatic peracid selected from performic, peracetic, perpropionic, or perbutyric acid.

7. The process of claims 1 or 2 in which an aromatic hydrocarbon capable of being iodinated is added to the reaction mixture to fix iodine released during the reaction.

* * * * *